United States Patent [19]

Kovacevic

[11] Patent Number: 5,158,095
[45] Date of Patent: Oct. 27, 1992

[54] MACHINE AND METHOD FOR TESTING EXERTED EFFORT WITHOUT PATIENT MALINGERING EFFECTS

[75] Inventor: Nebojsa Kovacevic, Plymouth, Minn.

[73] Assignee: N. K. Biotechnical Engineering Company, Minneapolis, Minn.

[21] Appl. No.: 711,964

[22] Filed: Jun. 7, 1991

[51] Int. Cl.$^5$ ............................................. A61B 5/103
[52] U.S. Cl. ...................................... 128/774; 73/379
[58] Field of Search .................. 128/774, 782; 73/379, 73/380, 381

[56] References Cited

U.S. PATENT DOCUMENTS

| | | | |
|---|---|---|---|
| 4,148,303 | 4/1979 | Cohen | 128/733 |
| 4,240,635 | 12/1980 | Brown | 273/138 A |
| 4,337,780 | 7/1982 | Metrick | 128/774 |
| 4,774,966 | 10/1988 | Lemmen | 128/774 |
| 4,949,729 | 8/1990 | Haski | 128/774 |

Primary Examiner—Max Hindenburg
Assistant Examiner—Guy V. Tucker
Attorney, Agent, or Firm—Kinney & Lange

[57] ABSTRACT

An apparatus and method for insuring that the evaluation of forces generated from an injured human limb or hand are accurately determined without malingering factors. The apparatus includes a sensor for determining forces generated by a hand which provides an output signal for input into a scaling circuit of a computer. The scaling circuit has a random scale factor randomly selected by a computer's microprocessor. The random scale factor alters presentation of the sensor output signals on a visual display. The visual display provides an indication to the patient of the amount of force that has been generated, but the scale factor modifies the output signals in a manner and amount that is unknown to the patient. The scale factor for example can be such that at a start of a test sequence a standard force can be displayed in approximately the middle of a scale shown on the visual display. In the next test of the sequence, the scale factor modifies a second set of test results so that the patient believes performance has increased. In a third test, the scale factor again modifies a third set of test results so that the patient believes performance has decreased. In this manner the test results can be analyzed and averaged with certainty as to whether or not the test results are valid, or if they are invalid by analyzing the test scores obtained at different scaling factors.

18 Claims, 2 Drawing Sheets

MACHINE AND METHOD FOR TESTING EXERTED EFFORT WITHOUT PATIENT MALINGERING EFFECTS

BACKGROUND OF THE INVENTION

The present invention relates to a machine for testing physical capabilities of a human test subject; more particularly, a machine and method are disclosed for testing and evaluating the strength of an injured human extremity without influences from the test subject distorting the test results.

The physical capabilities of a human are difficult to measure. Often these capabilities are needed in medical related circumstances. For example, if a person has suffered an injury to an extremity such as a hand, it is usually necessary to ascertain the extent of this injury in order to determine compensation. Other instances include the continued measurement of a person's capabilities during physical therapy. In this situation, the data obtained is instrumental in ascertaining the patient's progress, as well as the effectiveness of the therapy.

Although information regarding the physical capabilities of a person is valuable for the above-cited reasons, obtaining accurate data or test results is difficult. The accuracy of the data depends directly upon the cooperation of the individual. If the individual, either consciously or unconsciously, does not put forth sincere efforts during testing, the data obtained has little value. Lack of a sincere effort is called "malingering". The primary objective of all testing is to eliminate, or at least substantially reduce, malingering effects.

One factor that can influence test results is the visibility of a scale or indicator to the subject. The direct reading of the scale can result in meeting a certain level of effort without having it represent a maximum effort.

In an attempt to minimize malingering effects, evaluators have established a variety of testing procedures. Usually, these procedures require the individual performing the test to alter or vary the test instrument. For example, in hand strength assessment tests, the individual may be required to change or vary placement of the test instrument in the injured hand or, in the alternative, may be required to rapidly transfer the test instrument from one hand to another.

Both of these methods require constant manipulation of the test instrument by the test individual or patient. This manipulation can frustrate the patient, thereby questioning the accuracy of the results obtained. Moreover, these methods assume the individual is unable to learn and, thus, control the tests. Given the repetitious nature of testing in order to acquire comparative test results, this assumption is questionable.

Consequently, a need exists for an improved method of assessing physical capabilities. This new method should be easy to administer, and provide accurate verifiable test results, even if a malingering test subject is under study. The method thus cannot be predictable and must "fool" a malingerer.

SUMMARY OF THE INVENTION

The present invention provides an apparatus and method to fulfill the aforementioned physical assessment needs. Testing is carried out by continuous interaction of a test patient or subject with a visual display which does not represent the same scale during a test sequence. The same movement of an indicator of the visual display represents different values in a series of individual tests so that the patient has no idea if his or her performance has changed with respect to any preceding tests. Since a malingering patient, one that attempts to control physical performance either consciously or unconsciously, will be apt to adjust performance based on displayed results, the present invention provides an excellent system for insuring the validity of test results because the displayed results represent different quantities in each test.

The present invention relates to an apparatus and method for testing a physical capability of the patient, which include the operative steps of: (a) having the patient actuate a sensor in a test sequence that comprises a series of individual tests to provide output test signals that have values proportional to test efforts; (b) providing the generated test signals to a scaling circuit; (c) providing an output scaling factor of the scaling circuit to a visual display device to display relative values of each of the series of tests; and (d) changing the scaling factor in a random sequence between each of the tests.

In the preferred embodiment, the apparatus comprises a computer connected to the sensor to receive the proportional test output signals. A microprocessor within the computer initiates the scaling circuit to generate the random scale factor and controls transmission of both the random scale factor and test output signals to the visual display device. The patient observes the visual display to gauge his or her test performance. The scaling factor can be the output of a random number generator of known design.

DETAILED DESCRIPTION OF THE PREFERRED EMBODIMENTS

Figure 1:
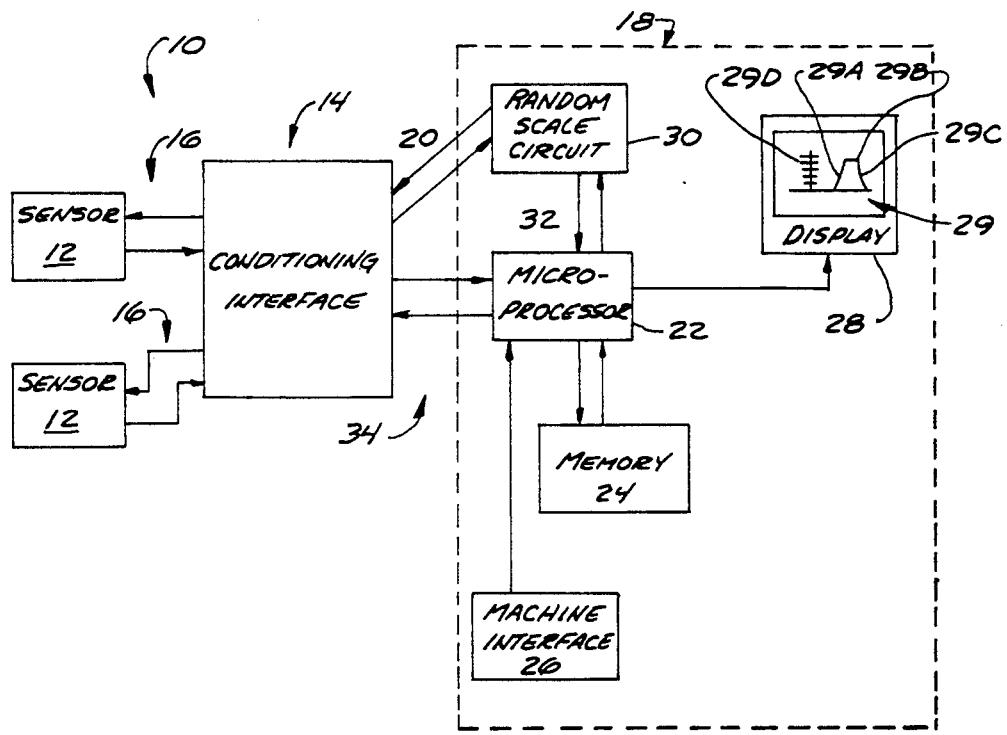
FIG. 1 is a block diagram of an apparatus in accordance with the present invention.

An apparatus for implementing the present invention is illustrated generally in FIG. 1 at 10. Apparatus 10 comprises at least one sensor 12, a conditioning and interface module 14 connected to sensor 12 with first signal lines 16, and a computer 18 connected to interface module 14 with second signal lines 20. Lines represented at 20 can be multiple lines as needed for carrying the signals.

Sensor 12 is preferably a test instrument used to assess physical attributes or impairments of a human test subject or patient. Such sensors can measure either the test subject's response to a particular stimuli or direct physical capabilities like the amount of force that can be generated, range of movement or the patient's overall dexterity. For a particular extremity like a hand, these instruments include grasp or pinch sensors. The grasp sensor measures and provides an output signal relative to the mount of gripping strength developed by the hand. The pinch sensor, functioning similar to that of the grasp sensor, measures and provides an output signal relative to the amount of force generated between the fingers and thumb of the hand. As shown in the preferred embodiment of FIG. 1, a plurality of test instruments or sensors 12 are provided. This arrangement allows comparative assessments to be made between like extremities such as between the left and right hands. Output signals from each sensor 12 are applied to a respective signal line 16.

Each signal line 16 is connected to interface module 14. Interface module 14 conditions the output signals by providing proper amplification and noise filtration before subsequent transmission to computer 18. If necessary or desired, interface module 14 provides control signals back to sensor 12 also on signal line 16. If sensor 12 is not self-powered, interface module 14 will further provide excitation signals. Interface module 14 or computer 18 will detect actuation of sensors 12 and the presence of output test signals. The interface module is preferably a circuit for providing excitation voltage to strain gages used for measuring force. The sensor outputs are generally analog voltage so the condition interface will include an A/D converter. A typical grasp sensor usable is shown in co-pending U.S. patent application Ser. No. 07/587,978, filed Sept. 25, 1990, now U.S. Pat. No. 5,125,270.

Interface module 14 is connected to computer 18 with second signal lines 20. Computer 18 comprises a control processor 22, commonly known as a microprocessor connected to associated memory 24 for program and data storage. A machine interface 26, preferably a keyboard, but which could be a function pad, or the like, is connected to microprocessor 22 for operator interaction.

As shown in the block diagram of FIG. 1, microprocessor 22 controls not only the various input signals from the sensors 12 and operator interface 26 as discussed above, but also controls a visual display device 28 which displays the relative values of sensor 12 output signals. Visual display 28 is a real time display in that input signals caused by actuation of sensor 12 are displayed with no intended delay. In the preferred embodiment, the relative output signals from sensor 12 are displayed on a graphical display having a suitable scale which the test subject or patient can associate with physical performance in the test. The scale is oriented such that with increased performance, be it the amount of force generated or the range of movement, the patient perceives displacement of a bar or cursor along the scale, as is well known. Although numerical displays could be substituted for each of the sensor outputs, a graphical or pictorial display is substantially easier to comprehend when all that is desired is a relative indication of test performance. The display can be a curve form 29 that shows the rise time 29A, peak value 29B, fall time 29C and time between the beginning and end of each test. A force scale indicator 29D also can be provided, but with no numbers.

As shown in FIG. 1, computer 18 further includes a random scaling circuit 30. Random scaling circuit 30 connects to microprocessor 22 with data lines 32, and provides as an output a random scale factor or signal gain factor. The random scale factor is initiated by microprocessor 22 from its operating software. During assessment testing, the random scale factor is determined by a conventional random number generator, and modifies visual display device 28 by providing an output signal which alters the display scale. Alternatively, the computer 18 receives the signals from the sensor and applies the scaling factor to the signals. In the preferred embodiment, random scale circuit 30 comprises a hardware circuit electrically connected to microprocessor 22 with data signal lines 32. In the alternative, interface module 14 is connected directly to microprocessor 22 with signal lines 34. Random scale circuit 30 would then comprise a software algorithm located in the computer's memory 24 which generates random scale factors used at appropriate times.

Figure 2:
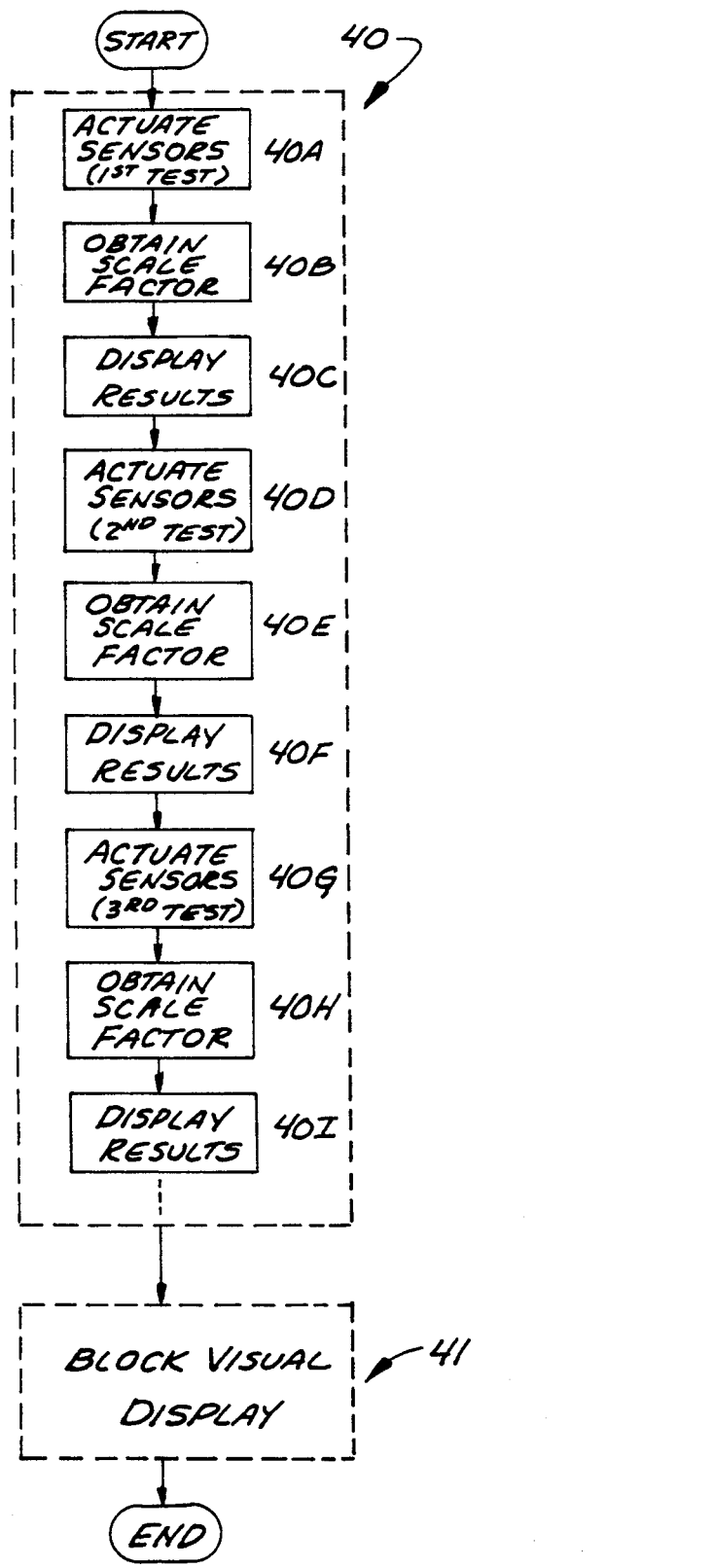
FIG. 2 is a flow chart illustrating a test method for operating the apparatus of FIG. 1.

FIG. 2 illustrates in block diagram form operation of apparatus 10 according to a testing procedure 40, used to assess a patient's physical capabilities. Specific individual steps of testing procedure 40 are as follows:

Step 40A—After the patient has been provided with sensors 12 of FIG. 1, the patient actuates the sensors in a test sequence (squeezing the grip sensors) which provide output signals that have values relative to the efforts put forth. When the testing procedure 40 is an assessment of the patient's hand strength, appropriate grip strength sensors are provided for each of the patient's hands. Output signals from these sensors when operated in the preset sequence would be relative to forces generated by each of the patient's hands.

Step 40B—Output signals from sensors 12, after proper interfacing and conditioning are then provided to computer 18. As shown in FIG. 1, these output signals either can be provided directly to microprocessor 22 or, alternatively, to scaling circuit 30.

Regardless of the method of input, scaling circuit 30 or the micro-processor 22 provides the random scale factor used in displaying the output signals on visual display 28. The random scale factor is initiated by the microprocessor from the microprocessor's operational software. The random scale factor determines relative placement of the output test signals on visual display device 28 and, therefore, how the patient will perceive his or her performance. The display will provide an indication of force generated that is observed by the patient. In the preferred embodiment for the first series of output signals received, a scale factor is chosen to place these test signals in the middle of the scale appearing on visual display device 28. In other words, the first generated output value or values becomes a standard which the patient will use consciously or unconsciously as a gauge to measure subsequent performance. The middle of the scale is chosen in order to convey that the patient's performance can increase or decrease in the subsequent tests.

Step 40C—The selected scale factor and output signal values are provided to visual display device 28. The patient observes his or her performance in real time, or in other words concurrently as the sensors are actuated.

Step 40D—The patient discontinues actuation of the sensors to indicate the end of a first test and to relax the grip or pinch and then again actuates the sensors to produce a second set of generated output signals. As with the first set of output signals, the second set have values that are relative to the amount of effort put forth.

Step 40E—The second set of output signals are received by computer 18, whereupon microprocessor 22 provides a second random scale factor from scaling circuit 30. The second random scale factor has a value that will change the scale of the output to provide an increase or decrease in the visual display for the same level of signal from the sensor. For example, if the second set of output signals have actual values that are equal to the standard (first) values measured in step 40B and the scale factor was also equal to that selected in step 40B, then the patient would observe that his or her performance was the same as in step 40A. However, the scale factor selected in this step is selected deliberately to convey a visual indication of either an increase or decrease in performance regardless of the actual performance of the patient. In the preferred embodiment, the scale factor is modified or chosen so that the second values are placed higher on the display scale. If the second set of values in fact equaled the standard values, the middle of the scale on the display would now correspond to values of less magnitude and the standard signal would be higher on the display.

Step 40F—The second scale factor and second set of generated output signals are provided to visual display device 28. The patient observes the indicator of the display. Although the patient perceives a difference in performance, the patient is unaware that the scale has in fact changed or, if aware, has no way of knowing what the change is. The second set of scaled values, like the first set of values, can be displayed on display device 28 as the sensors are actuated. Therefore, if the patient is prone to malingering influences, the patient may attempt to alter his or her performance. The actual exerted force values are provided from the conditioning interface on signal lines 34 or from the computer and will be recorded, so the examiner will know what the patient is doing.

Step 40G—The patient again actuates the sensors to produce a third set of generated output signals. Like the preceding sets of output signals, the third set has signal values from the sensor that are relative to the amount of effort put forth.

Step 40H—As in steps 40B and 40F, the signals are provided to computer 18 for display on visual display 28. However, once again a scale factor is randomly chosen so the patient cannot visually match performance in the third test to that of the other tests. The scale factor is changed from that of the first test in step 40A, and the second test in step 40D. In the preferred embodiment, the scale factor is selected such that a reduction in test performance is perceived for the same sensor output. If the third set of actual values were to equal the standard values, the third set of values would be displayed below the middle of the scale. In this third test, the middle of the scale corresponds to a force of greater magnitude than the previous tests.

Step 40I—The third scale factor and third set of generated output signals are provided to visual display device 28. The patient observes his or her performance concurrently, but does not know the scale factor. As before, if the patient attempts to control his or her performance to match that of the preceding tests, the patient will be fooled.

The aforementioned sequence is repeated until a sufficient amount of data is obtained. In each test, a different randomly selected scale factor is provided to visual display device 28 in order to mislead the patient. The scale factors can be selected at random or chosen in selected sequences to increase and decrease the scale.

In the preferred embodiment as shown in FIG. 2, a second sequence of tests 41 are performed. Test sequence 41 is the same as test sequence 40 described above, except that the patient is prevented from observing his or her performance on visual display 28. Test sequence 41 provides data that is independent of visually inspired malingering influences.

Data obtained from each test sequence 40 and 41 is then correlated with the corresponding scale factor to obtain the actual forces generated by the patient. Since a malingering patient will attempt during testing to generate forces that visually appear to agree, and since this patient is also unaware of the scale factors from one test to another, test data results will be free of intentionally weighted influence. In other words, a valid test of a patient's physical strength exists if results from each test are substantially equal to each other, even when the visual scale varies.

Although the present invention has been described with reference to preferred embodiments, workers skilled in the art will recognize that changes may be made in form and detail without departing from the spirit and scope of the invention.

What is claimed is:

1. A method of conducting a test to determine efforts exerted by a patient on a sensor comprising the steps of:
   providing a sensor for the patient;
   having the patient actuate the sensor in a test sequence comprising a series of tests to provide test signals having values proportional to test efforts;
   modifying a scale appearing on a visual display with a scaling factor;
   displaying the values of the test signals relative to the modified scale of the visual display to the patient for each of the series of tests; and
   selecting the scaling factor randomly between each of the tests.

2. The method of claim 1 and including the process of running at least three different tests of randomly selected different scaling factors.

3. An apparatus for providing test results indicating patient malingering input comprising:
   a sensor to measure and provide output test signals for each test of a series of tests having values proportional to test efforts by a patient;
   computer means connected to the sensor for receiving the output signals for each test, the computer means comprising scaling means for providing a scale factor that is different for each test in the series of tests, and microprocessor means coupled to the scaling means, the microprocessor means initiating generation of each scale factor;
   a display coupled to the microprocessor means, the display receiving the scale factor and the corresponding output signals, the display modifying a scale using the scale factor and displaying visual representations of the output signals with respect to the scale.

4. The apparatus of claim 3 wherein the scaling means provides random scale factors.

5. The apparatus of claim 3 wherein the scaling means provides scale factors in a selected sequence.

6. The apparatus of claim 3 wherein the scaling means comprises a software algorithm for generating said scale factor located in memory of the computer means.

7. An apparatus for providing test results indicating patient malingering input comprising:
   a sensor to measure and provide signals for each test of a series of tests having values proportional to test efforts by a patient;
   computer means for receiving the signals from the sensor and applying a scaling factor to the signals, the computer means having microprocessor means for providing the scaling factor wherein the scaling factor is selected to mislead the patient; and
   a display coupled to the microprocessor means and receiving the signals after the corresponding scaling factor has been applied, the display providing visual representations of the values of the signals whereby the representations viewed by the subject appear different for test signals that are substantially equal.

8. A method of conducting a test to determine efforts exerted by a patient on a sensor comprising the steps of:

providing a sensor for the patient;

having the patient actuate the sensor in a test sequence comprising at least two tests to provide test signals for each test having values proportional to test efforts;

displaying the values of the test signals to the patient on a visual display for each of the series of tests using a scale factor for each test which misleads the patient; and selecting at least two different scaling factors during the series of tests so that for values of one test substantially equal to values of another test a different scaling factor is used so that the respective values for each test are displayed differently on the visual display.

9. The method of claim 8 wherein the test is a force test to measure force exerted by a patient, and wherein the step of providing a sensor comprises providing a force sensor, and wherein the step of having the patient actuate the sensor provides test signals having values proportional to exerted forces.

10. The method of claim 9 and including the step of correlating the scaling factor to the individual tests to obtain a representation of actual force exerted in each of the tests.

11. The method of claim 8 wherein the test is a force test for manual hand operation, and wherein the step of providing a sensor comprises providing first and second sensors for measuring forces generated by each of a person's hands in a preset sequence to provide test signals having values that are proportional to force efforts by each hand.

12. The method of claim 8 and including the step of having the patient observe the visual display during testing procedures for a first predetermined number of tests, and performing the same sequence of tests while preventing the patient from observing the visual display during testing procedures.

13. The method of claim 8 wherein the step of selecting the scaling factors includes selecting each scaling factor in a selected sequence during the series of tests.

14. The method of claim 8 wherein the step of selecting the scaling factors includes selecting the scaling factor randomly during the series of tests.

15. The method of claim 8 wherein the step of selecting the scaling factors includes selecting the first scaling factor such that when the test signals from the first test are displayed on the visual display during the step of displaying, the test signals appear at a selected position on the visual display.

16. The method of claim 15 wherein the step of selecting the scaling factors includes selecting the second scaling factor such that for values representative of test signals of the second test substantially equal to the values representative of test signals from the first test, during the step of displaying, the values representative of test signals from the second test appear at a position other than at the selected position.

17. The method of claim 8 wherein the step of displaying includes applying the scaling factor to the test signals.

18. The method of claim 8 wherein the step of displaying includes modifying a scale appearing on the visual display with the scaling factor.

* * * * *